United States Patent
Gannoe et al.

(10) Patent No.: US 6,488,693 B2
(45) Date of Patent: Dec. 3, 2002

(54) VASCULAR INCISOR AND METHOD

(75) Inventors: James R. Gannoe, Redwood City, CA (US); Meir Moshe, El Sobronte, CA (US)

(73) Assignee: Hearport, Inc., Redwood City, CA (US)

( * ) Notice: Subject to any disclaimer, the term of this patent is extended or adjusted under 35 U.S.C. 154(b) by 0 days.

(21) Appl. No.: 09/813,256

(22) Filed: Jan. 26, 2001

(65) Prior Publication Data

US 2002/0002376 A1 Jan. 3, 2002

Related U.S. Application Data

(60) Provisional application No. 60/178,188, filed on Jan. 26, 2000.

(51) Int. Cl.$^7$ ................................................. A61B 17/32
(52) U.S. Cl. ........................ 606/167; 606/170; 606/185; 604/164.12
(58) Field of Search ................. 606/1, 108, 151–153, 606/167, 170, 184, 185, 173, 182, 172, 159; 600/564–568; 604/164.01–164.03, 164.12

(56) References Cited

U.S. PATENT DOCUMENTS

| | | | | |
|---|---|---|---|---|
| 518,600 A | * | 4/1894 | Hallman | |
| 3,762,416 A | * | 10/1973 | Moss et al. | 606/159 |
| 4,444,184 A | * | 4/1984 | Oretop | 606/170 |
| 5,089,000 A | * | 2/1992 | Agee et al. | 606/170 |
| 5,176,695 A | * | 1/1993 | Dulebphn | 606/170 |
| 5,234,450 A | * | 8/1993 | Segalowitz | 606/159 |
| 5,620,456 A | * | 4/1997 | Sauer et al. | 606/185 |
| 5,651,781 A | * | 7/1997 | Grace | 606/1 |
| 5,695,504 A | * | 12/1997 | Gifford et al. | 606/153 |
| 5,709,697 A | * | 1/1998 | Ratcliff et al. | 606/170 |
| 5,776,156 A | * | 7/1998 | Shikhman | 606/170 |

* cited by examiner

*Primary Examiner*—Michael H. Thaler

(57) ABSTRACT

An improved vascular incisor and method for allowing a user to safely create an incision in a body lumen. The present invention provides an apparatus which can create an incision in a front wall of the ascending aorta while preventing the blade from creating an incision in surrounding body structures, such as the back wall of the ascending aorta. The incisor includes a surgical element such as a blade which is activated by an actuator. As the actuator is depressed, the blade is moved from a protected, retracted position to an exposed, deployed position. The exposed blade is pushed into a front wall of the ascending aorta to create an incision. As the actuator is depressed further, the blade is automatically moved to the retracted position to prevent the blade from incising the back wall of the aorta.

19 Claims, 20 Drawing Sheets

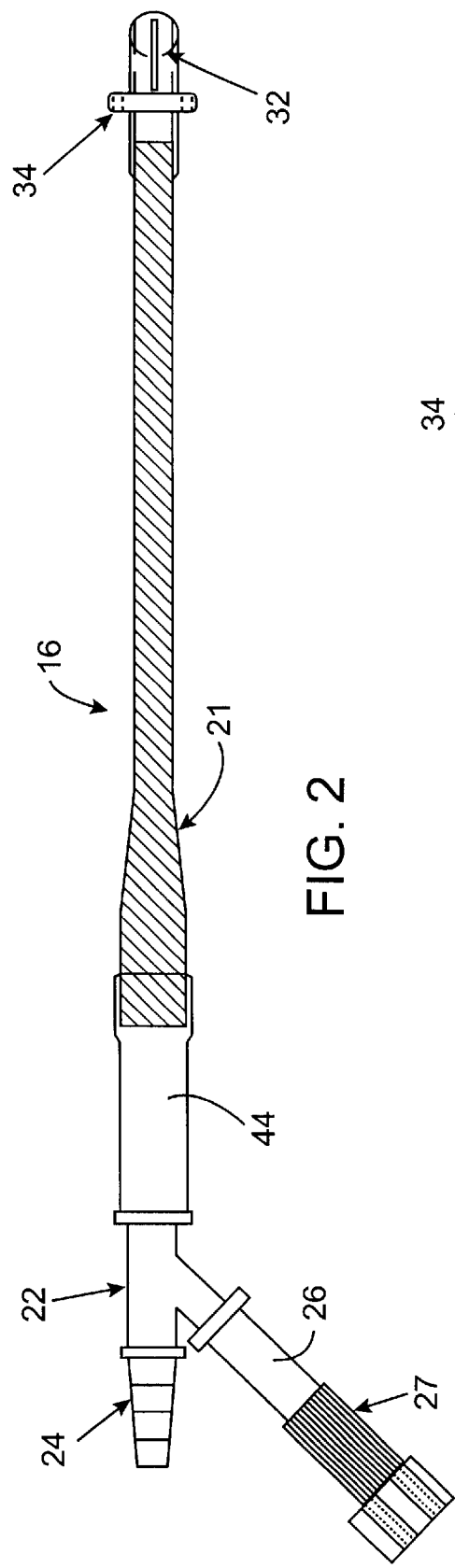
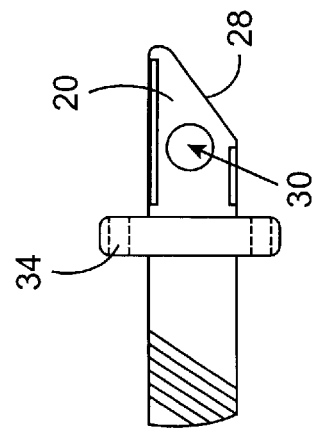
FIG. 2
FIG. 3

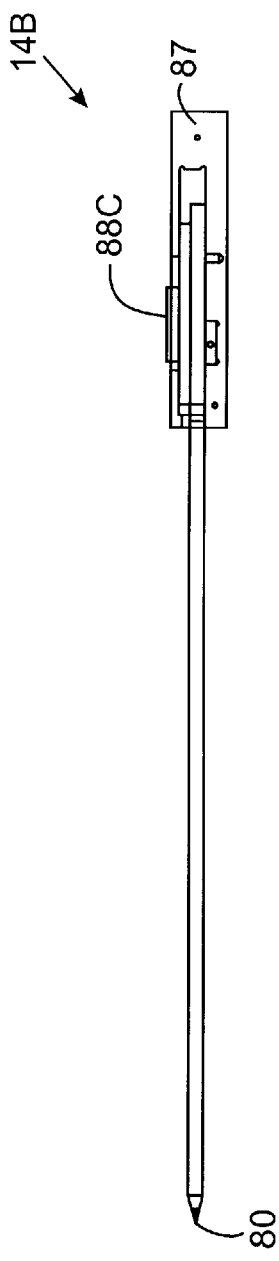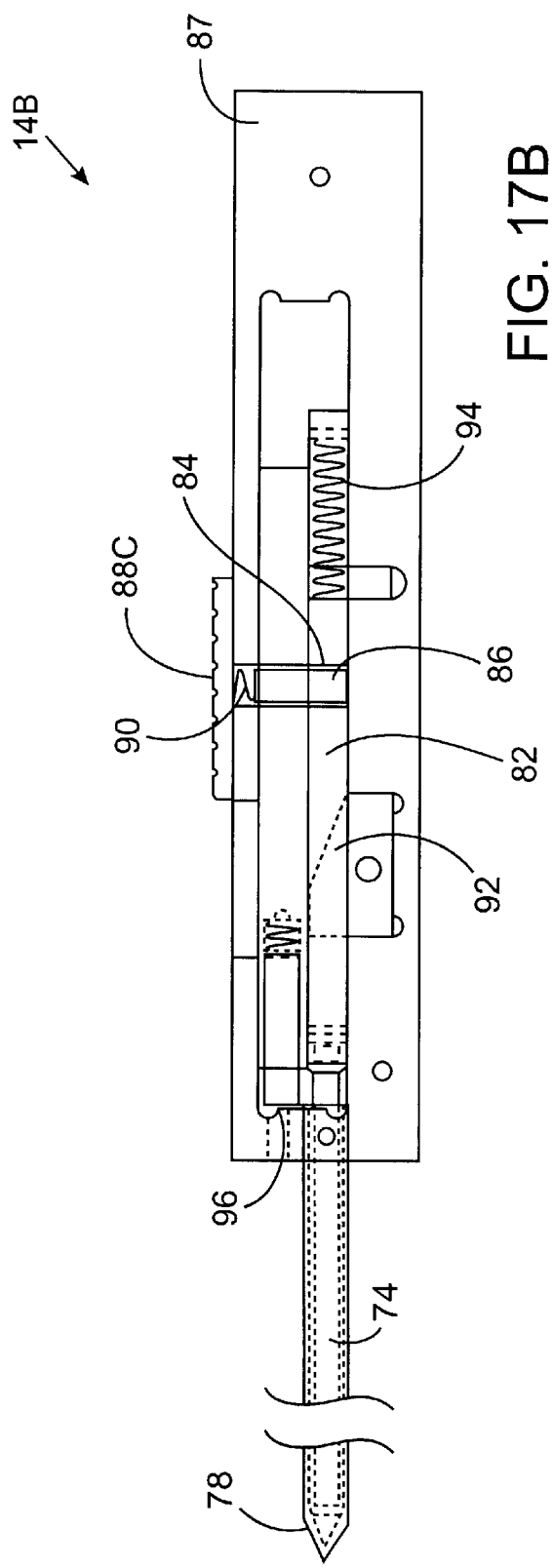

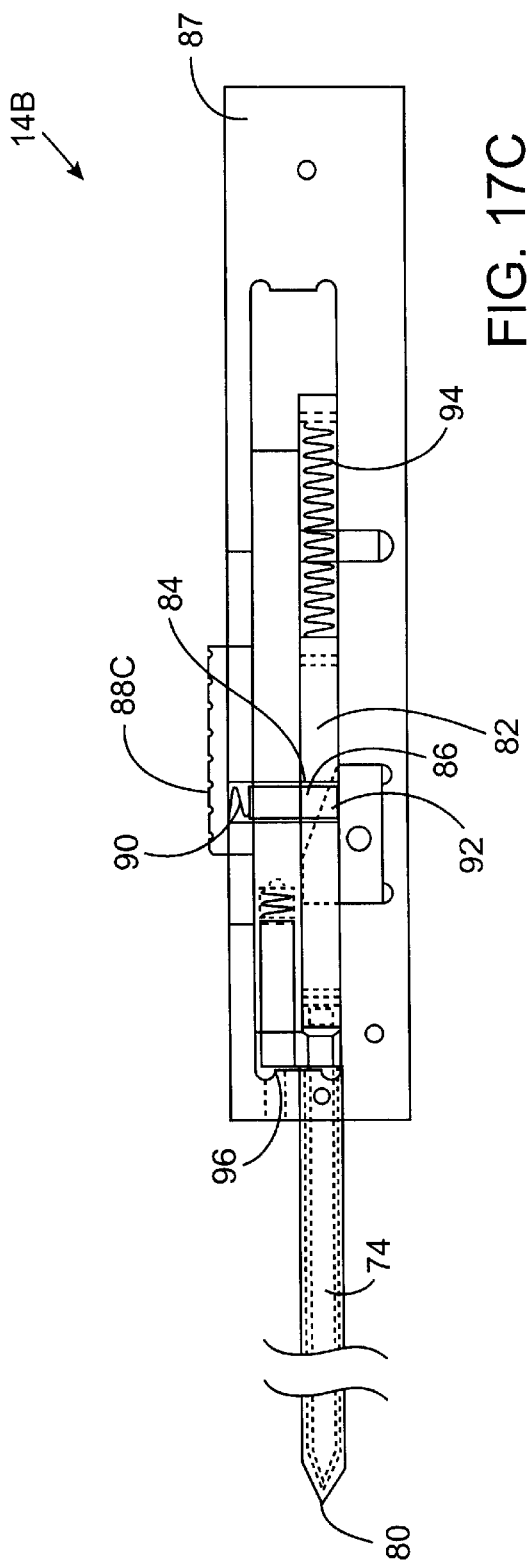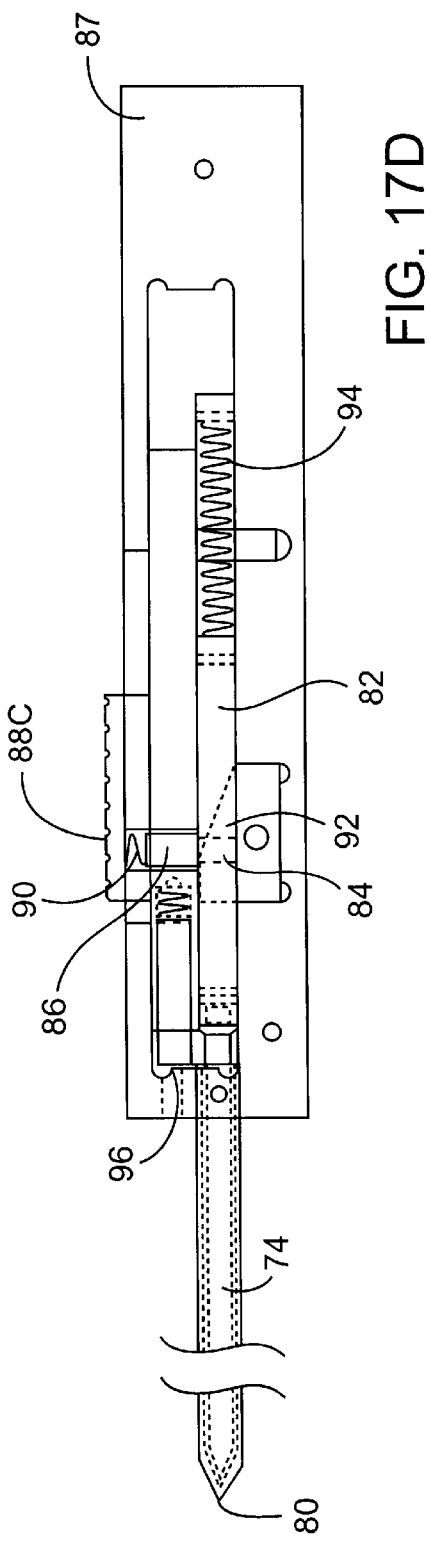

VASCULAR INCISOR AND METHOD

This application claims the benefit of Provisional application Ser. No. 60/178,188, filed Jan. 26, 2000.

BACKGROUND OF THE INVENTION

The present invention is directed to methods and devices for safely creating an incision through a wall of a patient's blood vessel. Such devices and methods are useful for performing various procedures on a patient's vascular system and heart such as the procedures described in U.S. Pat. Nos. 5,584,803 and 5,682,906 which describe coronary arty bypass grafting (CABG) and valve procedures, respectively.

Prior to occluding the ascending aorta and maintaining circulation of oxygenated blood, an incision must be made in the ascending aorta and a cannula inserted for return of blood to the patient. However, conventional methods suffer from potentially serious drawbacks. Conventional surgical techniques use a scalpel or knife to create an incision in the front wall of the ascending aorta prior to the insertion of the cannula into the aorta. Such scalpels have the potential to injure surrounding body structures. Additionally, in closed chest procedures, it is difficult and time consuming for the surgeon to separately manipulate both the scalpel and cannula.

Accordingly, there is a need for an incision method and device which can quickly and easily create an incision within the front wall of the ascending aorta through a small incision in the chest rather than a full sternotomy.

SUMMARY OF THE INVENTION

The present invention provides an improved vascular incisor, and cannula assembly and method for allowing a user to safely create an incision and insert a cannula in a body lumen. More specifically, the present invention provides an apparatus which can create an incision in a wall of the ascending aorta and insert a cannula in a fast and convenient single step process. The present invention includes a cannula and an incisor positionable within the cannula. The incisor has a blade which is moved by an actuator such as a trigger or a plunger. As the actuator is depressed, the blade is moved from a protected, retracted position to an exposed, deployed position. The exposed blade is pushed into a front wall of the ascending aorta to create an incision. As the plunger is depressed further, the blade is automatically moved to the retracted position to prevent the blade from contacting other body structures such as the back wall of the aorta. As the incisor is pushed through the incision, the cannula can be simultaneously inserted through the incision in a single step process.

In a first aspect, the present invention provides an incisor for creating a vascular incision. In one embodiment, the incisor has a rod which is movable relative to a body. A surgical element, such as a blade, is disposed at a distal end of the rod. A plunger having at least one finger engages a proximal end of the rod. When the plunger is moved from an undepressed position to a depressed position the rod and surgical element are advanced from the retracted position to the deployed position. The finger engages a ramp so that the fingers disengages from the proximal end of the rod, and the surgical element is moves back to the retracted position. In a specific configuration the incisor has a return spring to bias the plunger to the undepressed position. As the plunger is biased back to the undepressed position, the plunger fingers pass by the proximal surface of the push rod and the resilient spring force contained in the flexed plunger fingers biases the finger radially inward into the initial position and into engagement (or near engagement) with the proximal end of the push rod. At this position, the plunger and push rod are positioned for repeat actuation of the blade.

In another embodiment, the incisor includes a housing and a movable push rod. The push rod is biased toward a retracted position. Actuation of a trigger pin over a ramp moves the push rod and a surgical element from the retracted position towards a deployed position. When the trigger pin reaches a top of the ramp, the trigger pin disengages from the push rod and allows the surgical element and the push rod to return to the retracted position. In some embodiments, the trigger pin is coupled to an actuator, such as a trigger or a plunger. The actuator is actuated in the distal direction to move the trigger pin distally over the ramp. In one configuration, the actuator is biased towards an initial position so that after the surgical element has been deployed and retracted, the actuator is biased back to the initial position and the apparatus is ready for repeat actuation. In another specific configuration, the actuator is moved along a longitudinal axis of motion which is parallel to the longitudinal axis of the push rod. In yet another specific configuration, the actuator is two pivotal handles. The handles are movable between an initial outwardly separated position and a closed position in which the handles are adjacent to the body. A user squeezes the handles to the closed position to move the surgical element to the deployed position. In most configurations, the handles are biased to the initial position, such that when the handles are released, the handles return to the initial position and the incisor is ready for repeat actuation.

In yet another embodiment, the incisor has an elongate rod with a surgical element disposed at the far end of the rod. A rod spring biases the rod and surgical element in the retracted position. A hammer is positioned in the body, typically along an axis parallel with the push rod. Actuation of an actuator engages an angled cam surface against the hammer to move the hammer to compress a hammer spring. Once the trigger and cam surface move past the hammer, the cam surface disengages from the hammer so that the hammer spring can expand and push the hammer distally against the rod to move the surgical element to the deployed position. Because the rod and surgical element are biased in the retracted position by the rod spring, the surgical element is instantaneously pulled back to the retracted position.

In another aspect, the present invention provides methods of forming an incision in a tissue structure of a patient. In one method, a plunger is depressed substantially along a longitudinal axis of the device to move a surgical element from a retracted position to a deployed position. The surgical element is moved from the deployed position to the retracted position independently of further movement of the plunger. In most embodiments, the plunger is biased back to an undepressed position such that the plunger is ready for repeat actuation.

In yet another method, the present invention provides a method for inserting a cannula into a blood vessel. The method comprises positioning a tip of a device adjacent the blood vessel. An actuator is activated to move a surgical element from a retracted position to a deployed position. The surgical element is automatically moved from the deployed position to the retracted position while simultaneously inserting the cannula into the blood vessel. In most embodiments, the plunger is automatically returned to the undepressed position so that the plunger is ready for repeat actuation.

In yet another method, the present invention provides a method of creating an incision. The method comprises placing a distal tip of a device adjacent a vessel wall. An actuator is activated to compress a spring. The spring is expanded to deploy a surgical element to create an incision in a vessel. Thereafter, the surgical element is automatically retracted.

In yet another method, the present invention provides a method for occluding an aorta. A surgical element is deployed to create an opening in the aorta. The surgical element is automatically retracted and the cannula is inserted through the opening and into the aorta. The surgical element is withdrawn from the cannula and an aortic occlusion device is positioned in at least a portion of the aorta. In some methods, the aortic occlusion device includes an inflatable balloon which is expanded to occlude the aorta.

In still another aspect, the present invention provides an assembly for creating an incision in a blood vessel. The assembly includes a cannula having a lumen. An incisor having an automatically retracting surgical element is removably receivable within the lumen of the cannula. The cannula has a body and a push rod with a surgical element. An actuator is coupled to the push rod to move the surgical element between a retracted position and a deployed position. A fixed release mechanism is positioned within the body to disengage the push rod from the actuator to allow the push rod and surgical element to be biased from the deployed position to the retracted position.

In another embodiment, the assembly includes a cannula and an incisor having a hammer type assembly for retracting the surgical element. A hammer and hammer spring are positioned within the body and adjacent the push rod. A cam surface, typically coupled to an actuator, moves to compress the hammer and hammer spring. The cam surface is moved beyond the hammer and allows the hammer spring to expand so as to push the hammer distally against a push rod. The impulse from the hammer moves the surgical element from a retracted position to a deployed position. In most assemblies, the surgical element (and rod) are biased to the retracted position, such that the surgical element is immediately biased back to the retracted position.

In another embodiment, the present invention provides an assembly for treating the ascending aorta. The assembly includes a cannula having a lumen and an incisor having an automatically retracting surgical element. The incisor is removably received in the lumen of the catheter such that a surgical element is positioned near a distal end of the cannula to create an incision in the ascending aorta. An aortic occlusion device can be inserted through the lumen of the cannula and into the incision in the ascending aorta after the incisor has been removed from the cannula.

Other aspects, features, and advantages of the present invention will become apparent upon consideration of the following detailed description and the accompanying drawings.

BRIEF DESCRIPTION OF THE DRAWINGS

FIG. 2 shows the cannula;

FIG. 3 shows an enlarged view of the distal end of the cannula of FIG. 2;

FIG. 17A shows yet another embodiment of the incisor;

FIG. 17B shows the embodiment of 17B with the thumb switch in a proximal position and the surgical element in a retracted position;

FIG. 17C shows the thumb switch moving distally and the surgical element in a deployed position;

FIG. 17D shows the thumb switch in a distal position and the surgical element in the retracted position;

DESCRIPTION OF THE SPECIFIC EMBODIMENTS

Figure 1:
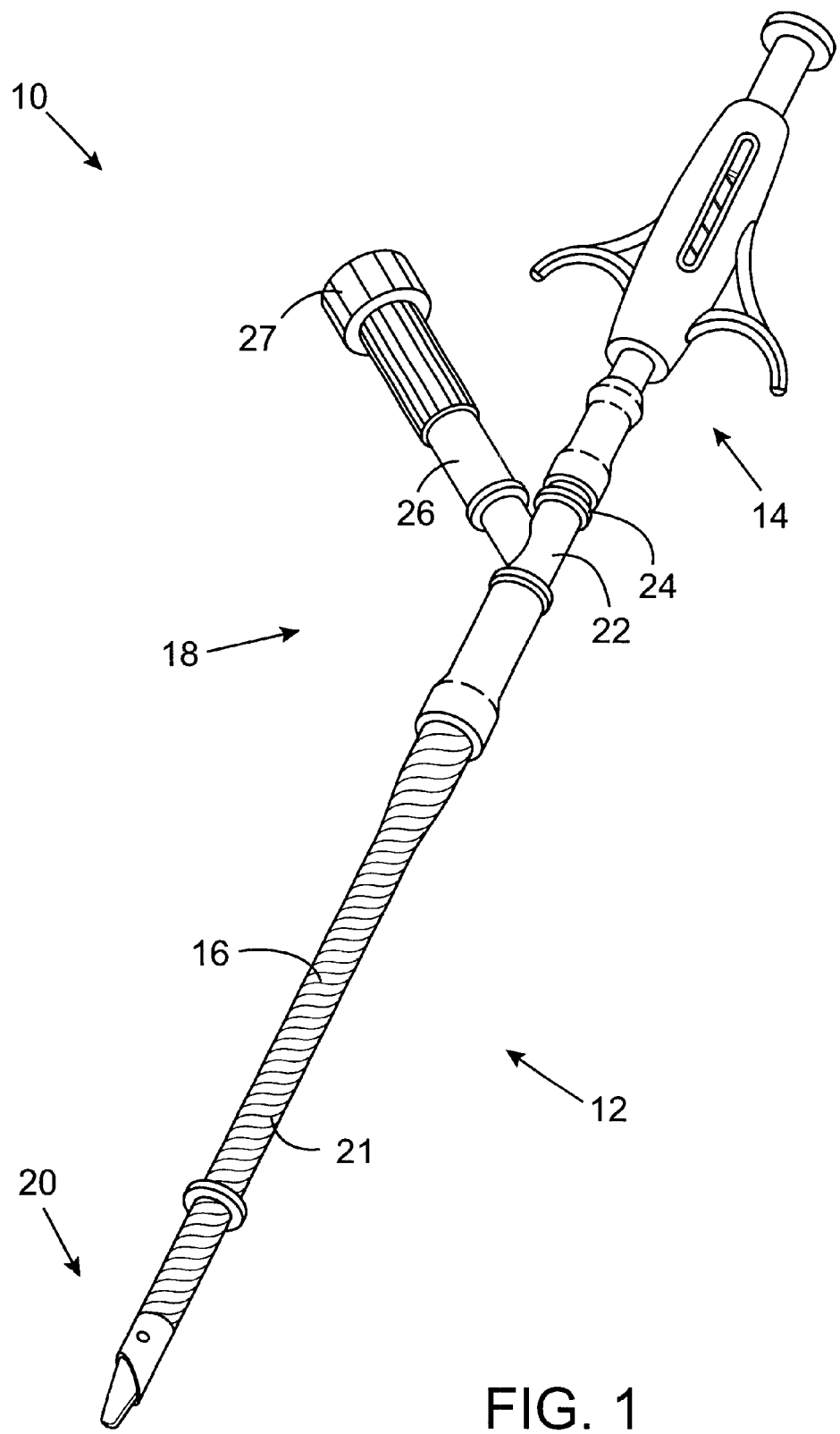
FIG. 1 is a perspective view of an incisor within a cannula.

Apparatus and methods according to the present invention will generally be adapted for creating an incision within a target area of a body lumen, usually in the ascending artery or other coronary arteries.

In preferred embodiments, systems according to the present invention will comprise incisors, cannulas, and aortic occluding devices having elongate bodies adapted for introduction into the body. The dimensions and other physical characteristics of the catheter bodies will vary significantly depending on the procedure performed. In an exemplary case, the cannula, incisor, and aortic occluding device bodies are flexible to allow introduction from the outside the patient's cavity to the target site in the aorta or the heart. In other embodiments, any or all of the devices may be partially or entirely rigid.

Cannula bodies will typically be composed of a biocompatible organic polymer which is fabricated by conventional extrusion techniques. Suitable polymers can be found in commonly owned U.S. Pat. No. 5,863,366, the full disclosure of which is incorporated herein by reference. Optionally, at least a portion of the cannula housing may be reinforced with braid, helical wires, axial filaments, or the like, in order to increase rotational strength, column strength, toughness, pushability, and the like. However, in some embodiments at least a portion of the lumen is not reinforced so that a clamp can be placed over the lumen to prevent the flow of body fluid (i.e. blood) up the lumen. A first arm of the cannula often has a keying feature, such as a colored marking, line, molded feature, or the like, which can promote proper alignment of the incisor with the cannula and with the aorta. In most embodiments, the combined weight of the cannula and incisor will be very light to facilitate easy manipulation and placement of the apparatus using one hand.

A surgical element, such as a cutting blade will be positioned at the distal end of the incisor. The cutting blades usually have at least two outwardly facing cutting edges and usually are formed from a metal such as stainless steel, but can also be formed from hard plastics, ceramics, or composites of two or more materials, which can be honed or otherwise formed into the desired cutting edge. In the exemplary embodiments, the cutting blades have a width which is approximately equal to the inner diameter of the cannula. For example, when incising the ascending aorta, the blades will typically have a width between approximately 4 mm and 6 mm. The larger blades have been found create a clean incision while minimizing tearing in the artery wall. In most embodiments, the blade will extend approximately 2 mm–6 mm past the distal tip of the incisor. Optionally, the cutting edges of the blades may be hardened, e.g. by chrome plating.

The incisor uses an actuator, plunger, trigger, or the like to actuate the deployment and retraction of the surgical element. In some embodiments, the trigger is movable along a parallel axis with the longitudinal axis of the cannula and incisor. Users can better control the deployment and retraction of the incising element when the trigger actuation direction is in the same direction as the deployment of the blade and insertion of the cannula. However, the present invention is not limited to such a configuration and in other embodiments alternative trigger configurations can be used.

While the remaining discussion will be directed toward creating an incision in the ascending aorta, it will be appreciated that the concepts of the present invention can be used to create an incision or perforation in a variety of other organs, vessels, and tissue structures.

Figure 5:
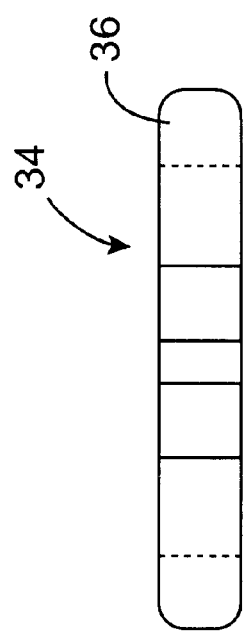
FIG. 5 is a side view of the ring of FIG. 4.
Figure 4:
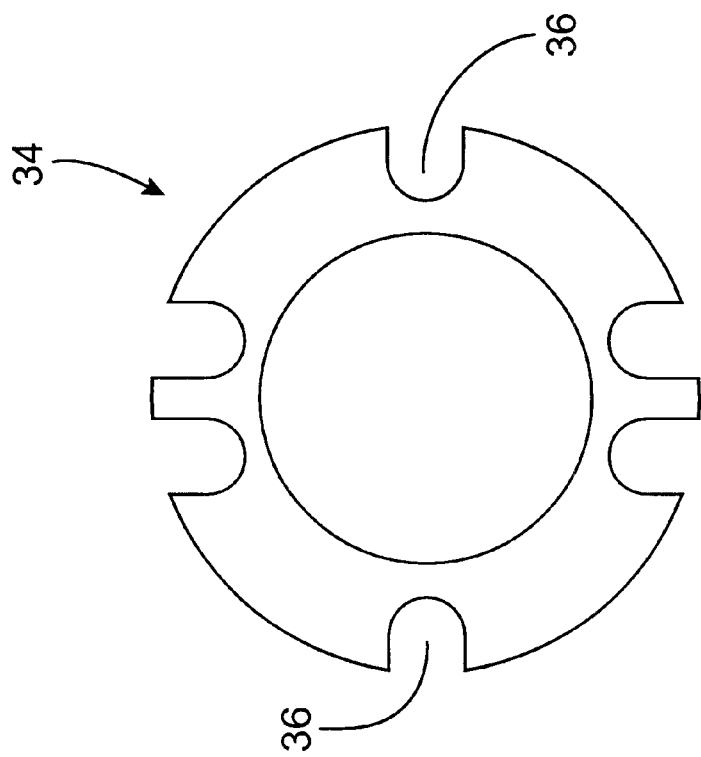
FIG. 4 is a plan view of a ring.

Referring to FIG. 1, a system 10 of the present invention comprises a cannula 12 and an incisor 14. As illustrated in FIGS. 1 and 2, the cannula 12 is typically used to return oxygenated blood to the patient when the patient's heart is arrested. The cannula comprises a lumen 16 having a proximal end 18 and a distal end 20. The lumen 16 has a reinforced section 21. The reinforced section 21 is preferably formed in the manner described in U.S. Pat. No. 5,863,366, which was previously incorporated by reference. A Y-arm connector 22 having a first arm 24 and a second arm 26 is fluidly coupled to the proximal end of the elongate lumen 16. The first arm 24 has an opening which can receive the shaft of the incisor 14. The second arm 26 has a hemostasis valve 27. The hemostasis valve 27 can be any of a variety of known hemostasis valves, but is preferably a Thouy-Borst valve. Referring now to FIG. 3, the distal end 20 of the cannula is angled and has a distal opening 28 and two side ports 30 for infusing oxygenated blood into the vasculature of the patient. Optionally, radiopaque markers 32 are provided at the distal end for visualization using fluoroscopy. As shown most clearly in FIGS. 4 and 5, a ring 34 is attached to the distal end 20 of the cannula 12. The ring 34 limits the depth of insertion of the cannula 12 into the vessel, stabilizes the cannula 12, and receives purse-string sutures within slots 36 to provide hemostasis around the cannula 12 when the cannula 12 is positioned in the vessel.

Figure 6:
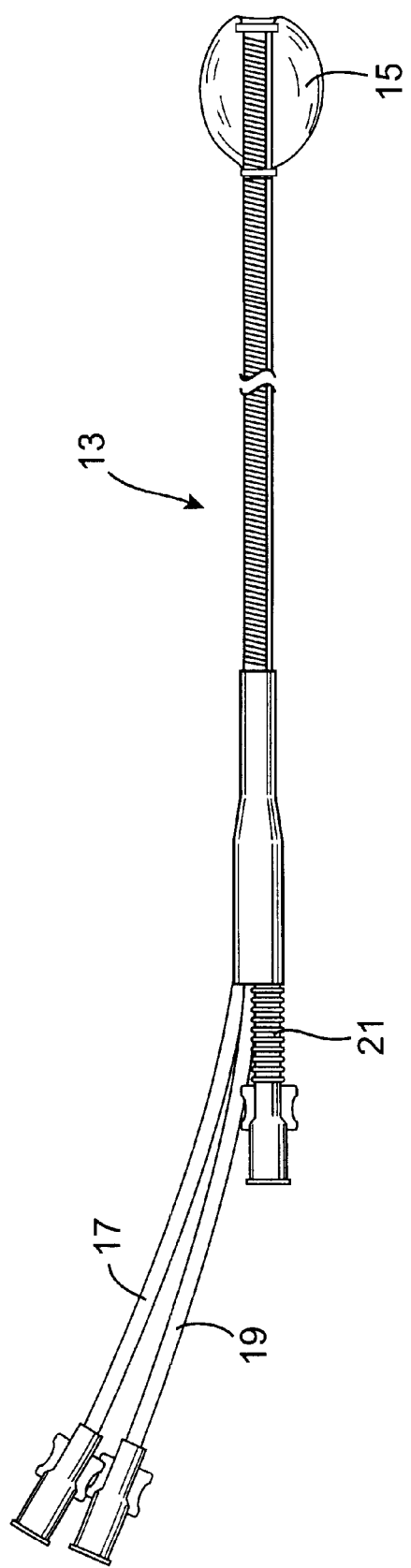
FIG. 6 show an aortic occluding device.

The system of the present invention includes, in a preferred embodiment, an aortic occlusion device for internal occlusion of the aorta. Referring to FIG. 6, one embodiment of an aortic occlusion device 13 is shown. The aortic occlusion device 13 has an occluding member 15 configured to occlude a patient's ascending aorta. The occluding member is preferably a balloon but may also be a mechanically actuated member. The aortic occlusion device 13 has an inflation lumen 17 for inflating the occluding member 15, a pressure lumen 19 for measuring pressure in the ascending aorta, and a lumen 21 for delivering cardioplegic fluid and/or venting the ascending aorta. The aortic occlusion device 13 can be manufactured in a manner such as extrusion, but is preferably manufactured and used as described in U.S. patent application Ser. No. 08/782,113, filed Jan. 13, 1997, the full disclosure which is incorporated herein by reference.

The aortic occlusion device 13 is preferably substantially straight in an unbiased position, however, the aortic occlusion device may also have a shaped end. For example, the aortic occlusion device can have a curved or an L-shaped end which facilitates positioning the occluding member 15 in the ascending aorta depending upon the surgical approach. The aortic occlusion device is preferably flexible so that it can be bent as necessary without kinking. A more complete discussion of the aortic occlusion device can be found in U.S. patent application Ser. No. 09/235,043, filed Jan. 21, 1999, the full disclosure of which is incorporated herein by reference. In use, the aortic occlusion device 13 can be introduced into the patient through the cannula 12. The cannula is positioned in a patient's ascending aorta with the aortic occlusion device 13 passing through the hemostasis valve 27 (FIG. 10).

Figure 7:
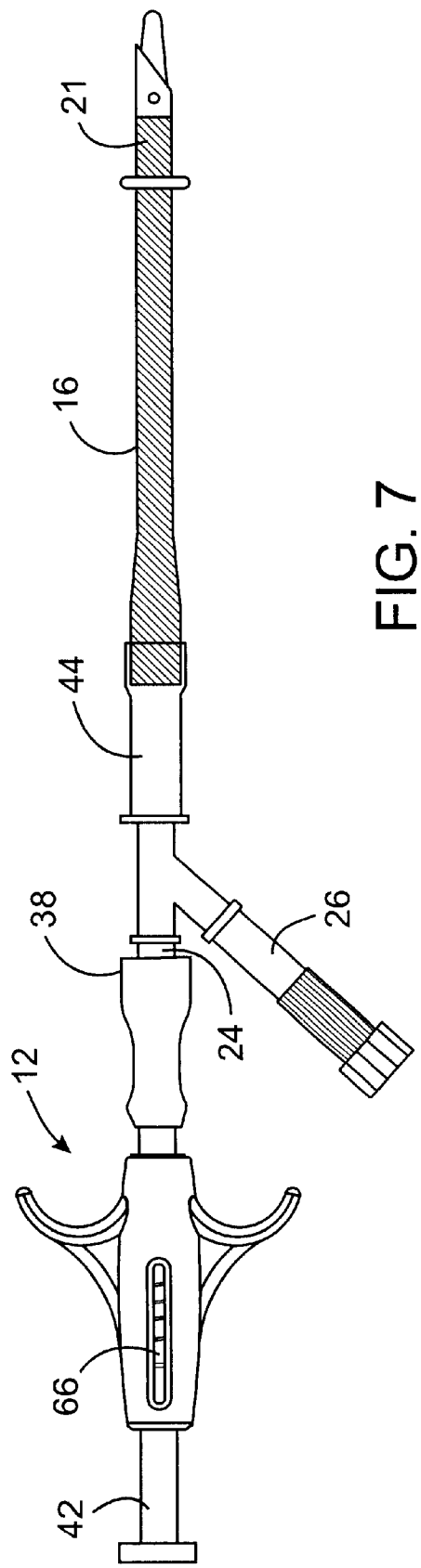
FIG. 7 shows the incisor disposed within the cannula and the incising element in a retracted position.
Figure 8:
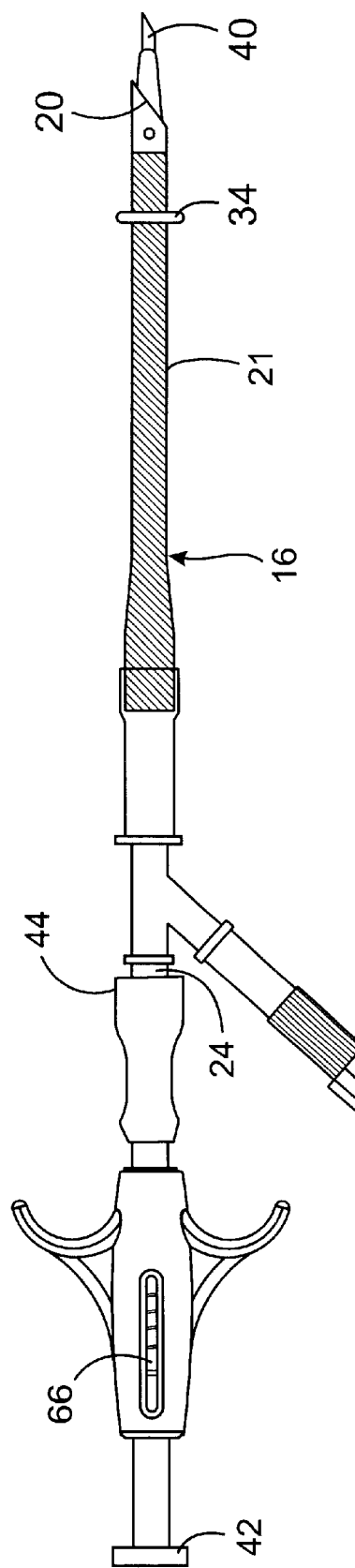
FIG. 8 shows the incisor disposed within the cannula and the incising element in a deployed position.

Referring now to FIGS. 7–8, an introducing incisor 14 is positioned in the cannula 12 to create an incision so that the cannula 12 and aortic occlusion device 13 can be introduced into the vessel. The incisor has a connector hub 38 which is received by the first arm 24 of the cannula 12 to provide a sealed connection between the incisor 14 and the cannula 12. The incisor 14 has an incising element 40 to create an incision in the wall of the vessel. The incising element 40 is attached to a push rod (not shown) which is coupled to a plunger 42 for moving the incising element 40 between the retracted position (FIG. 7) and the exposed position (FIG. 8). The incising element 40 is preferably biased in the retracted position and is only exposed when the plunger 42 is depressed by the user.

Figure 9:
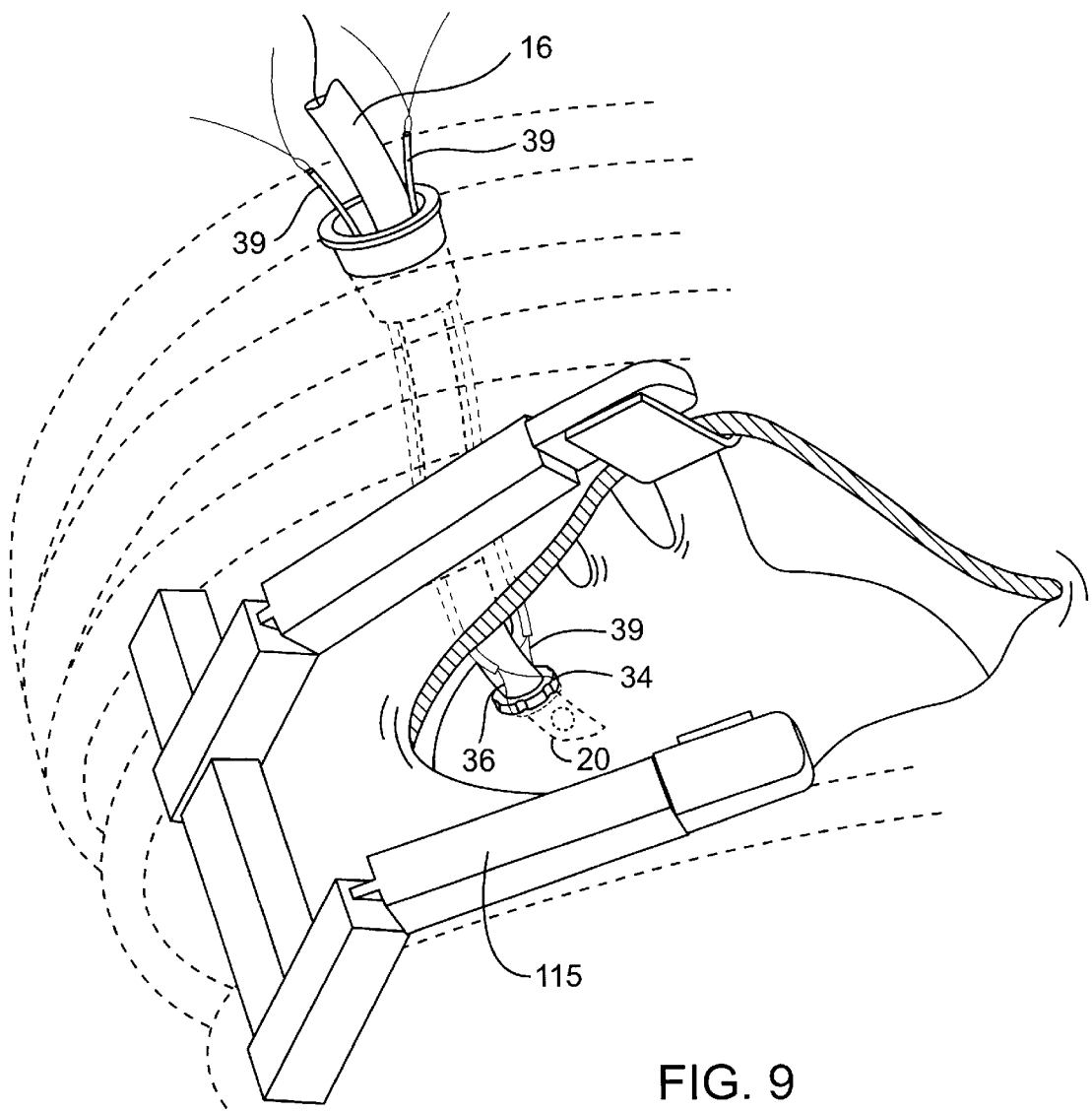
FIG. 9 shows the introduction of the cannula into the ascending aorta.
Figure 11:
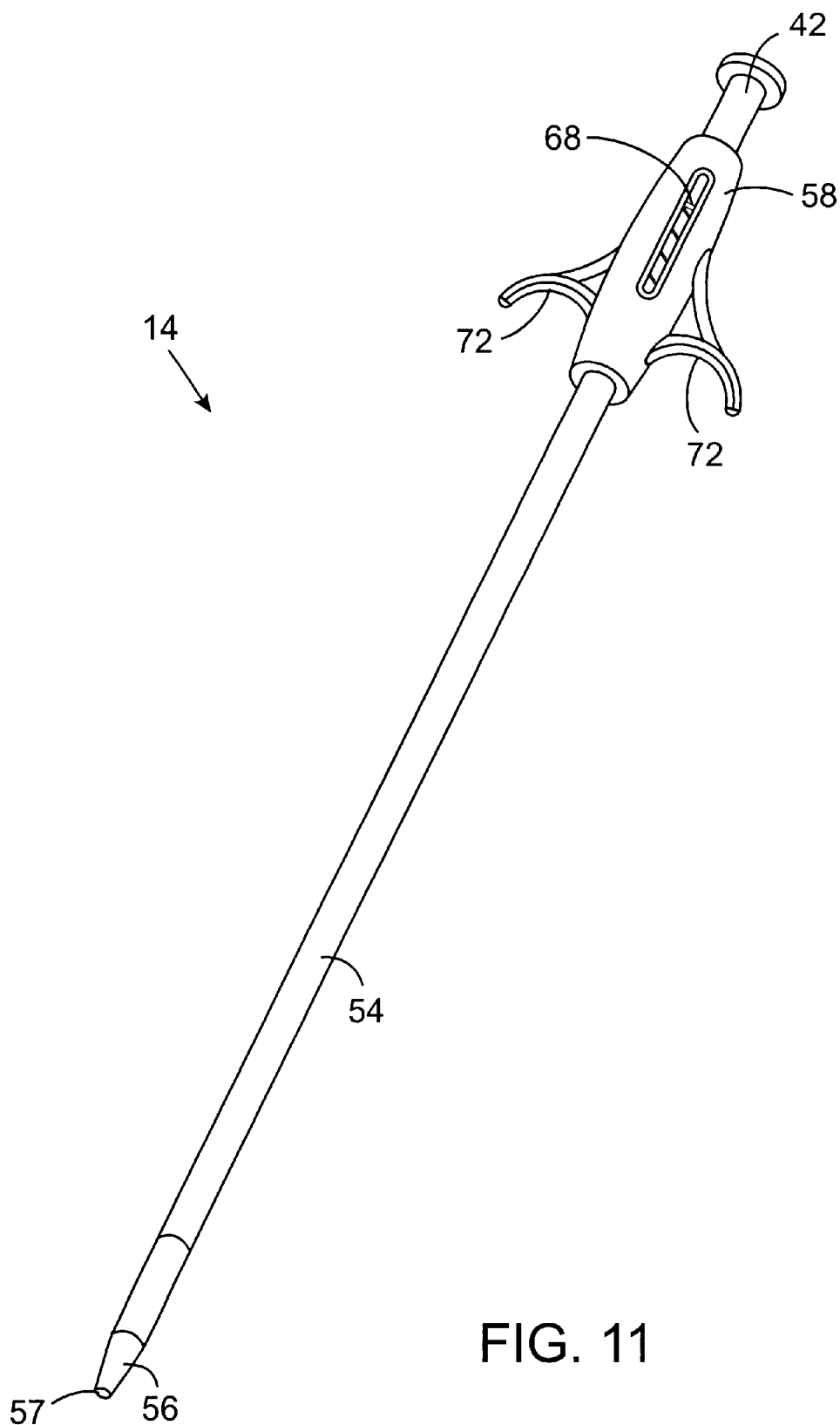
FIG. 11 is an exemplary embodiment of the incisor.

Generally, purse string sutures 39 can be sewn in the ascending aorta prior to advancing the cannula and incisor. The purse strings can provide hemostasis around the cannula (after it has been advanced into the aorta). The cannula and incisor are then moved adjacent an outer wall of the aorta. In some embodiments, the distal tip 56 of the incisor 14 can include traction features 57, such as a roughened surface, protrusions, or the like, which help maintain the distal tip within the purse string sutures (FIG. 11). Light pressure is applied to the incisor to create a dimple or indentation in the aorta so that the distal tip remains in a centered position within the purse strings when the incising element is advanced into aorta wall. After the incision is created, the cannula and incisor are advanced through the incision and into the aorta. The incising element is retracted as the trigger is advanced and the purse string sutures are tensioned around the cannula. The radiopaque marker at the cannula tip may be viewed under fluoroscopy and the cannula manipulated until the angled tip is directed toward the aortic valve (FIG. 9). The aortic occlusion device is then passed through the hemostasis valve and advanced until the occluding member is positioned in the ascending aorta. Delivery of oxygenated blood, occlusion of the ascending aorta, and delivery of cardioplegic fluid is then performed in the manner described in U.S. Pat. No. 5,584,803, the full disclosure of which is incorporated herein by reference.

Figure 10:
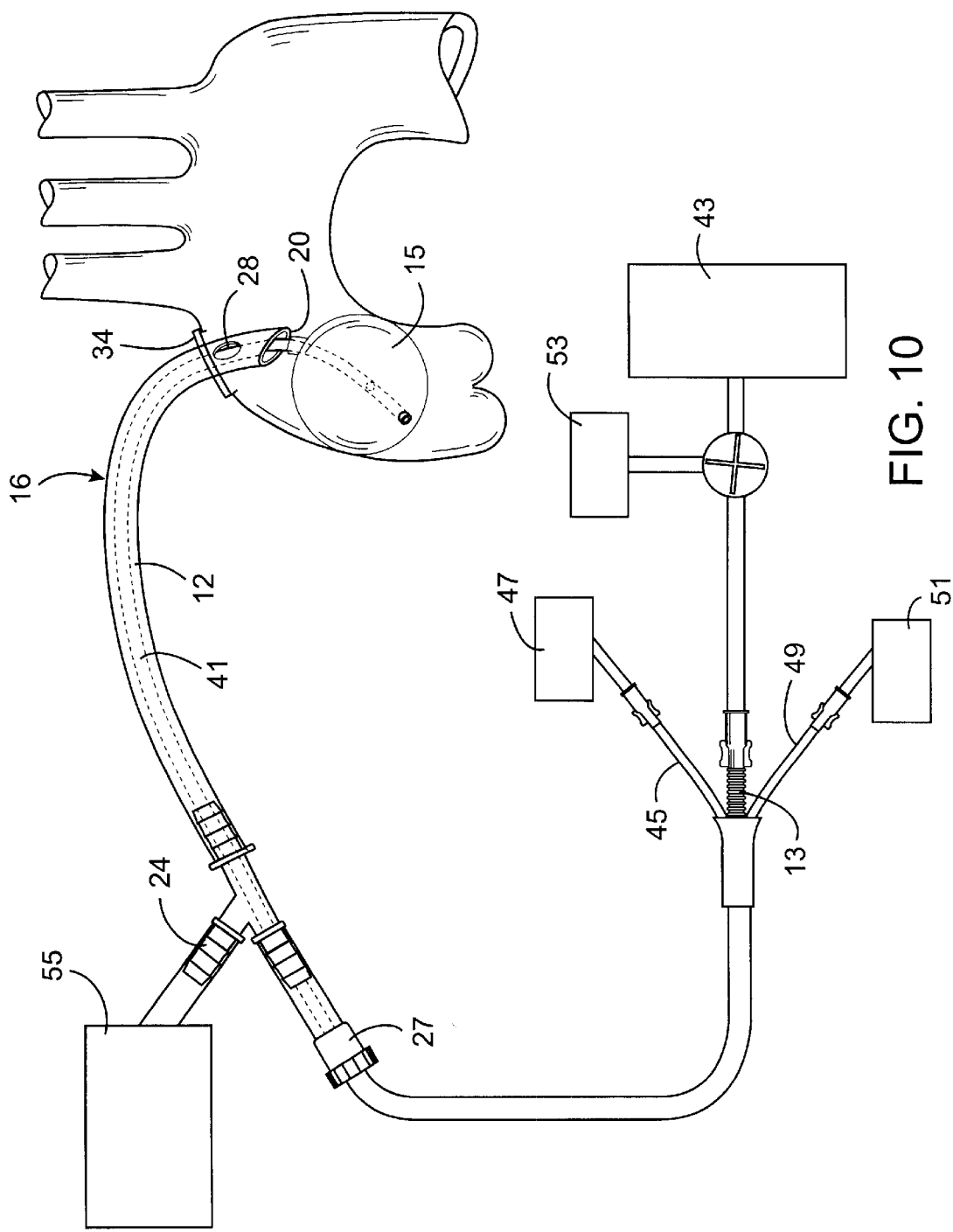
FIG. 10 shows the aortic occlusion device and cannula passing through an incision in the ascending aorta.

As shown in FIG. 10, the lumen 21 of the occlusion device is coupled to a source of cardioplegic fluid 43, the inflation lumen 15 is coupled to a source of inflation fluid 47, and the pressure lumen 19 is coupled to the pressure monitor 51 for measuring pressure in the ascending aorta. The lumen can also be coupled to a vacuum source 53 for venting the ascending aorta.

The first arm 24 of the cannula is coupled to a source of oxygenated blood 55 so that blood is delivered through the lumen of the cannula with the blood passing through the annular region between the cannula 12 and the aortic occlusion device.

Figure 12:
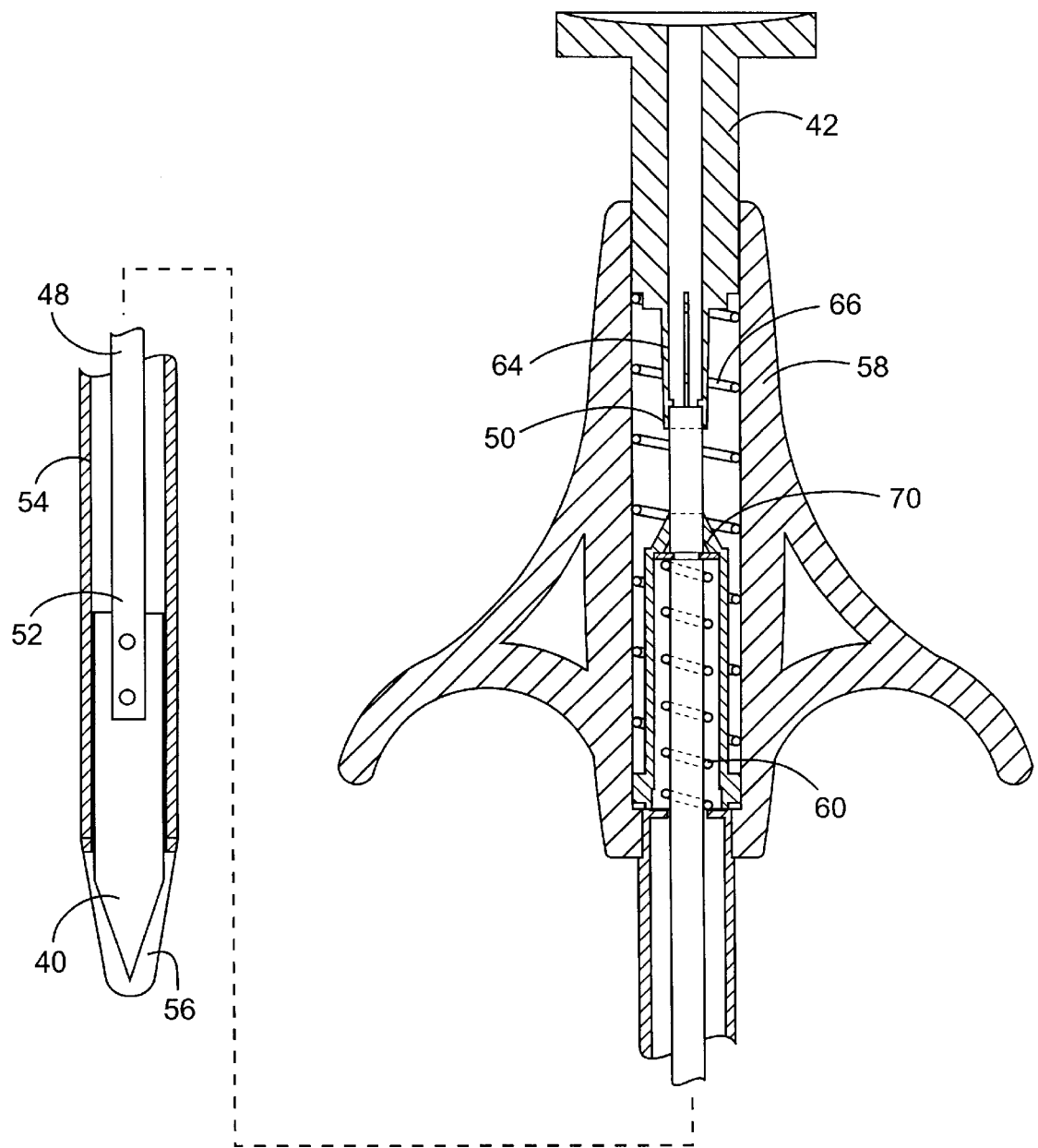
FIG. 12 is a cross-sectional view of the structure of the incisor of FIG. 11 with the plunger in an undepressed position and the incising element in a retracted position.

FIGS. 11 and 12 illustrate an exemplary embodiment of an incisor of the present invention. The incisor 14 includes a push rod 48 having a proximal end 50 and a distal end 52. The push rod is rigid enough to transmit a compressive force between the proximal and distal ends, but preferably is still flexible enough to advance through a curved cannula. A surgical element 40 such as a blade or incising element is attached to the distal end of the push rod 48, while the proximal end of the push rod has a surface or enlarged push cap which can be engaged by at least one plunger finger (described in more detail herein below). An elongate housing 54 having a tapered or angled distal tip surrounds the push rod and incising element. An opening or slot within the angled distal tip 56 allows the surgical element to move from a retracted position to a deployed position. A body 58 having an opening which receives the proximal end 50 of the push rod 48 is attached to the proximal end of the elongate housing 54. A retraction spring 60 positioned within the body 58 is coupled to the proximal end 50 of the push rod 48 to bias the push rod 48 and surgical element 40 in the retracted position. A movable actuator 42, such as a plunger or trigger, releasably engages the proximal surface of the push rod. As will be described in more detail below, a ramp or cam surface 70 is disposed within a distal end of the body 58 to disengage the fingers 64 from the push rod as the plunger 42 moves toward the fully depressed position. Optionally, a set screw 68 can be attached to the plunger 42 to prevent the plunger 42 from rotating. Additionally, the set screw 68 can act as an indicator to inform the user how far the incising element has been deployed.

As illustrated in FIG. 11, in some configurations the body has two finger grips 72 which extend radially from the body 58 and a plunger 42 that extends proximally through an opening in the body 58. The incisor is grasped with the user's fingers like a hypodermic needle and is actuated with either the thumb or the palm of the hand. Such a configuration allows the user to manipulate the incisor with only one hand, while providing the user with enhanced control of the incisor.

Figure 13:
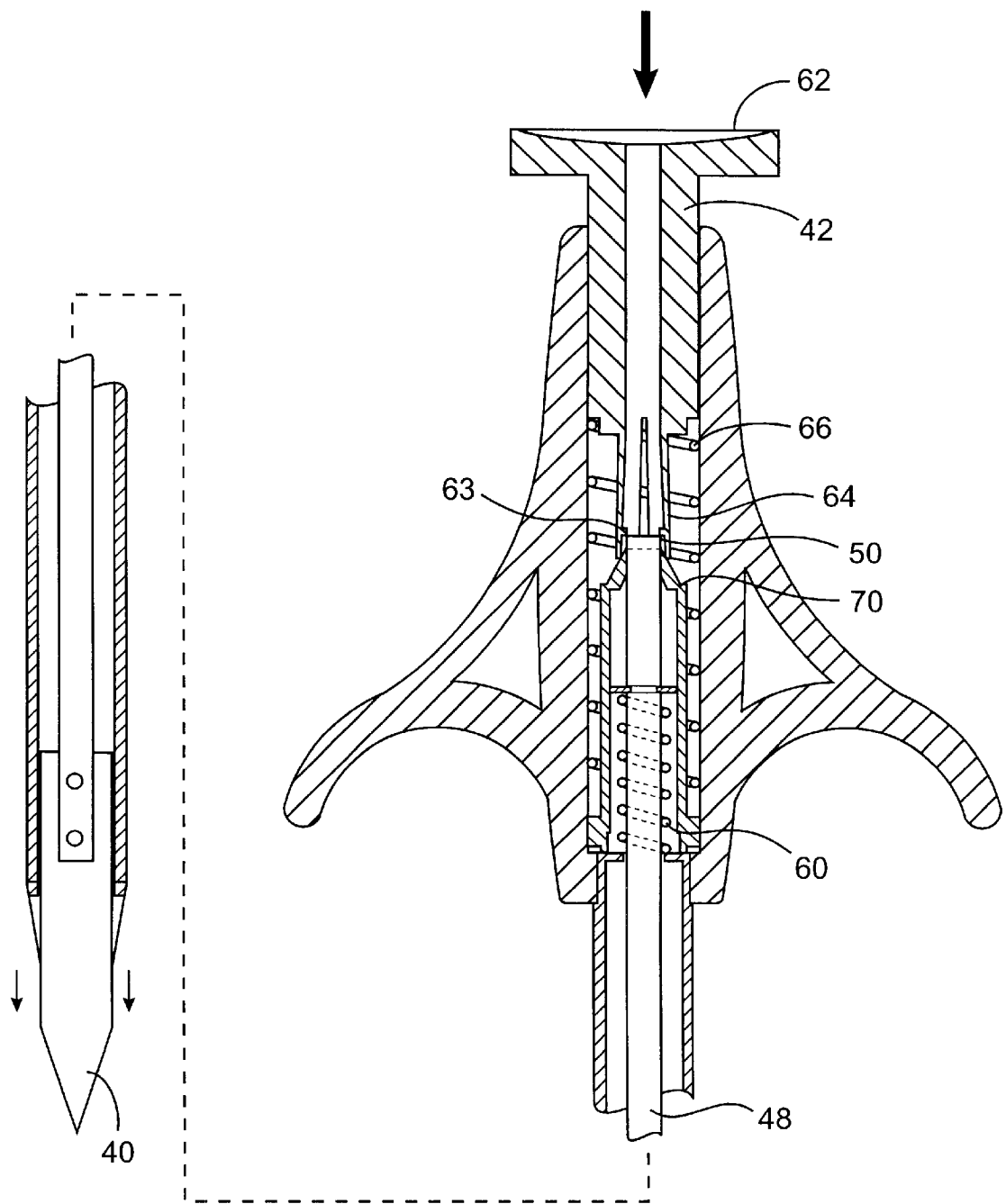
FIG. 13 is a cross-sectional view of the structure of the incisor of FIG. 11 with the plunger in a partially depressed position and the incising element in a deployed position.
Figure 14:
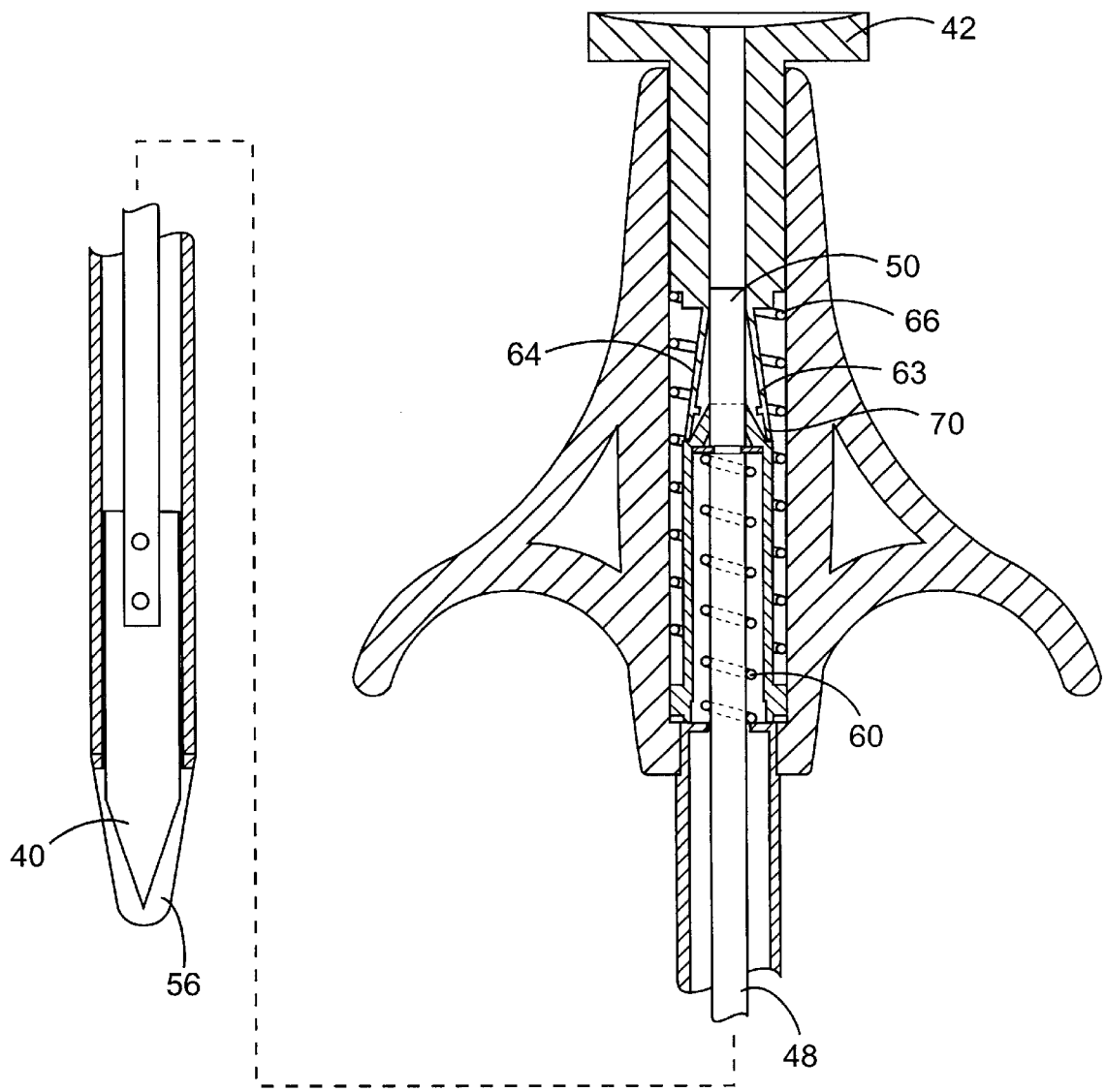
FIG. 14 is a cross-sectional view of the structure of the incisor of FIG. 11 with the plunger in a fully depressed position and the incising element in the retracted position.

As shown in FIG. 12 the plunger is maintained in the undepressed position by a plunger return spring 66, and the blade 40 is maintained in the retracted position within the distal tip 56 by the rod retraction spring 60. In the initial undepressed position the plunger finger(s) 64 may or may not contact the proximal end 50 of the push rod 48. As shown by the arrow in FIG. 13, the plunger is advanced by pushing on the engagement surface 62 to overcome the resistance of the return spring 66 and retraction spring 60. Protrusions 63 on the plunger finger(s) 64 contact and begin to push on the proximal surface 50 of the push rod. As the plunger 42 is advanced, the push rod 48 and surgical element 40 are advanced with the plunger. In most embodiments the push rod 48 and blade 40 are advanced at a 1:1 rate with the plunger 42, however, in other embodiments, the ratio can be modified. As the plunger nears the end of its path, a surface of the plunger finger(s) 64 engage the ramps 70. As the fingers advance over the ramps, the fingers 64 are urged radially outward away from the proximal end of the push rod. When the push rod 48 has been advanced to a fully deployed position, the ramp disengages the plunger finger(s) 64 from the proximal end of the push rod (FIG. 14). The retraction spring 60 then urges the push rod 48 (and surgical element 40) back to its initial, retracted position. In most embodiments, the release of the push rod will create an audible click to inform the user that the surgical element has been retracted.

As the plunger is released, the return spring 66 biases the plunger 42 back to the initial undepressed position (FIG. 11). As the plunger fingers 64 pass by the proximal surface of the push rod 48, the resilient spring force contained in the flexed plunger fingers bias the fingers radially inward to the initial position and into engagement (or near engagement) with the proximal end 50 of the push rod. At this position, the plunger and push rod are positioned for additional repeat actuation. Optionally, a locking mechanism may be provided to lock the plunger after a single actuation to prevent inadvertent repeat actuation.

Figure 15:
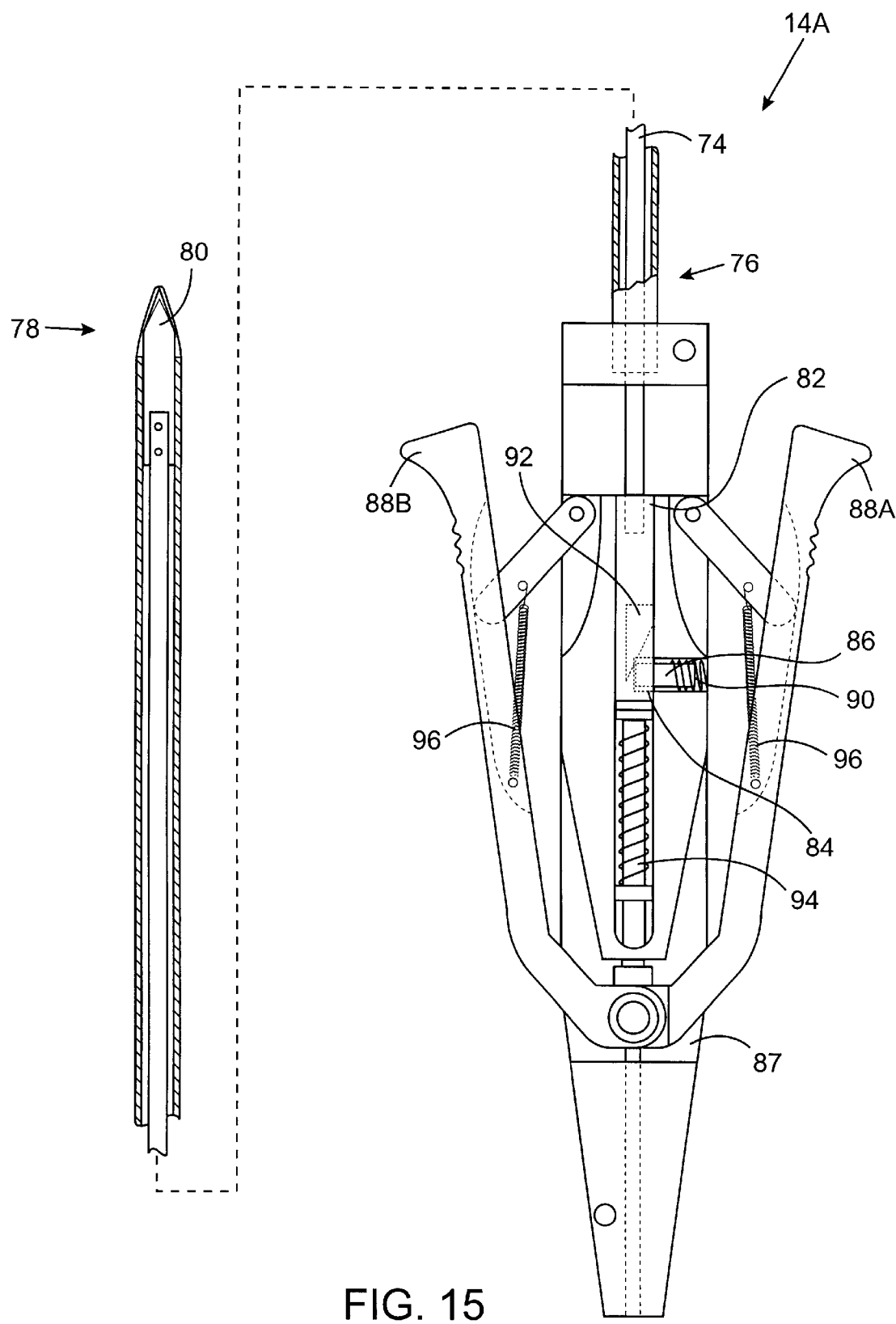
FIG. 15 is a cross-sectional view of another exemplary embodiment of an incisor with handles in an extended position and the incising element in a retracted position.
Figure 16:
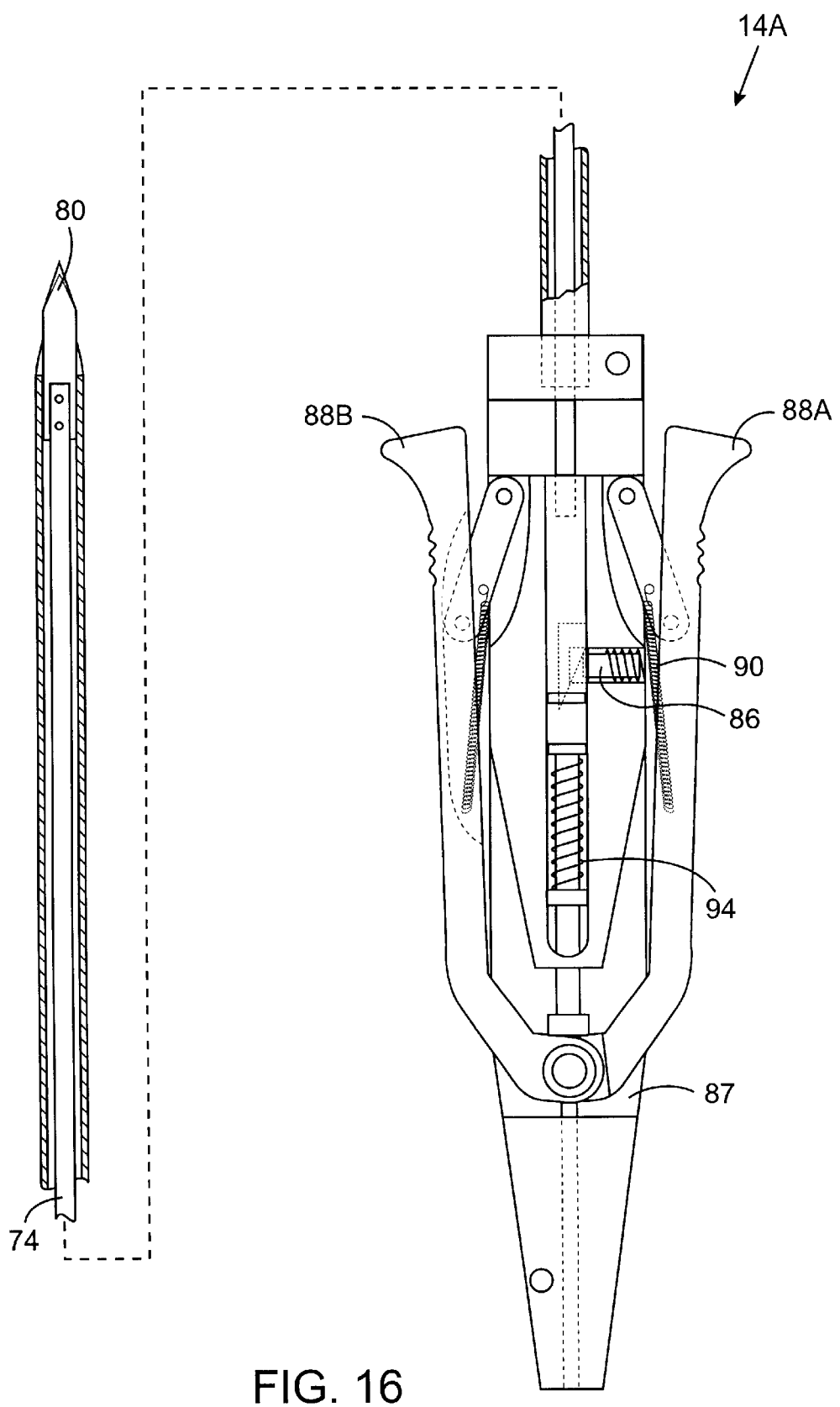
FIG. 16 is a cross-sectional view of the incisor of FIG. 15 with the handles in a closed position and the incising element in a deployed position.

FIGS. 15 to 16 illustrate another exemplary embodiment of the incisor 14A having an automatically retracting surgical element. The incisor 14A has a push rod 74 with a proximal end 76 and a distal end 78. An incising element 80 is attached to the distal end of the push rod and a return plate 82 is coupled to the proximal end of the push rod. Return plate 82 is movable distally and proximally relative to body 87. An aperture 84 in the return plate 82 is sized to releasably receive a trigger pin 86. In most configurations, the trigger pin 86 is biased with a compression spring 90 into the aperture 84 of the return plate 82. In most embodiments, handles 88 are pivotally coupled to body 87 and are linked to return plate 82 through the trigger pin. A ramp or cam surface 92 is disposed on the body adjacent the return plate 82 so that actuation of the handle 88 and trigger pin 86 move the return plate, push rod, and surgical element from the retracted position to the deployed position.

In use, a user actuates the handle (or actuator) 88 to move the return plate 82, push rod 74 and incising element 80 distally, thereby moving trigger pin 86 up the ramp 92. As the trigger pin 86 moves up the ramp 92, the trigger pin 86 begins to move out of the aperture 84 in the return plate 82. When the trigger pin 86 reaches the top of the ramp, the trigger pin is urged out of the aperture and disengages from the return plate 82. A return spring 94 then urges the return plate 82, push rod 74, and surgical element 80 back to the retracted position. When the user releases the handle 88, a trigger return spring 96 or an equivalent, urges the actuator and trigger pin back to its initial position. Because the trigger pin 86 is biased toward the return plate 82, the trigger pin is urged back into the aperture 84 and the device is ready for actuation.

In a specific configuration, the actuator comprises two pivotal handles 88A, 88B which are movable between an extended position in which the handles are outwardly separated and a closed position in which the handles are adjacent the body. Handle springs 96 bias the handles in the extended position and automatically return the handles to the extended position after each actuation. When the handles are squeezed together, return plate 82 is advanced distally and the trigger pin 86 is moved up the ramp, as described above.

As illustrated in FIGS. 17A to 17D, in another specific configuration of the incisor 14B, the trigger comprises a linearly actuated thumb trigger 88C which moves along an axis which is substantially parallel to the longitudinal axis of the blade rod. Actuation of the trigger in a distal direction moves the surgical element distally. The distal motion of the trigger has been found to be more natural since the distal movement of the trigger coincides with the distal advancement of the blade and the distal advancement of the cannula through the incision.

As shown in FIGS. 17A and 17B, the incisor 14B has a push rod 74 with a proximal end 76 and a distal end 78. An surgical element 80 is attached to the distal end of the push rod and a return plate 82 is coupled to the proximal end of the push rod. Return plate 82 is movable distally and proximally relative to body 87. An aperture 84 in the return plate 82 is sized to releasably receive a pin 86. In most configurations, the pin 86 is biased with a compression spring 90 into the aperture 84 of the return plate 82. Thumb switch 88C is slidably attached to body 87 and is coupled to return plate 82 through the pin 86. As shown in FIG. 17C, a ramp or cam surface 92 is disposed on the body adjacent the return plate 82 such that actuation of the thumb switch 88 and trigger pin 86 move the return plate 82, push rod 74, and surgical element 80 from the retracted position to the deployed position. As the pin 86 nears its most distal point, the ramp engages the pin and the pin 86 begins to move out of the aperture 84 (FIG. 17C). When the pin 86 reaches the top of the ramp, the pin is urged completely out of the aperture. The pin 86 disengages from the return plate 82 and a return spring 94 urges the return plate 82, push rod 74, and surgical element 80 back to the retracted position. When the user releases the thumb switch 88C, a return spring 96 or an equivalent, urges the thumb switch 88C and pin back to their initial position. Because the pin 86 is biased by spring 90 toward the return plate 82, the pin is urged back into the aperture 84 and the incisor is ready for repeat actuation.

Figure 18:
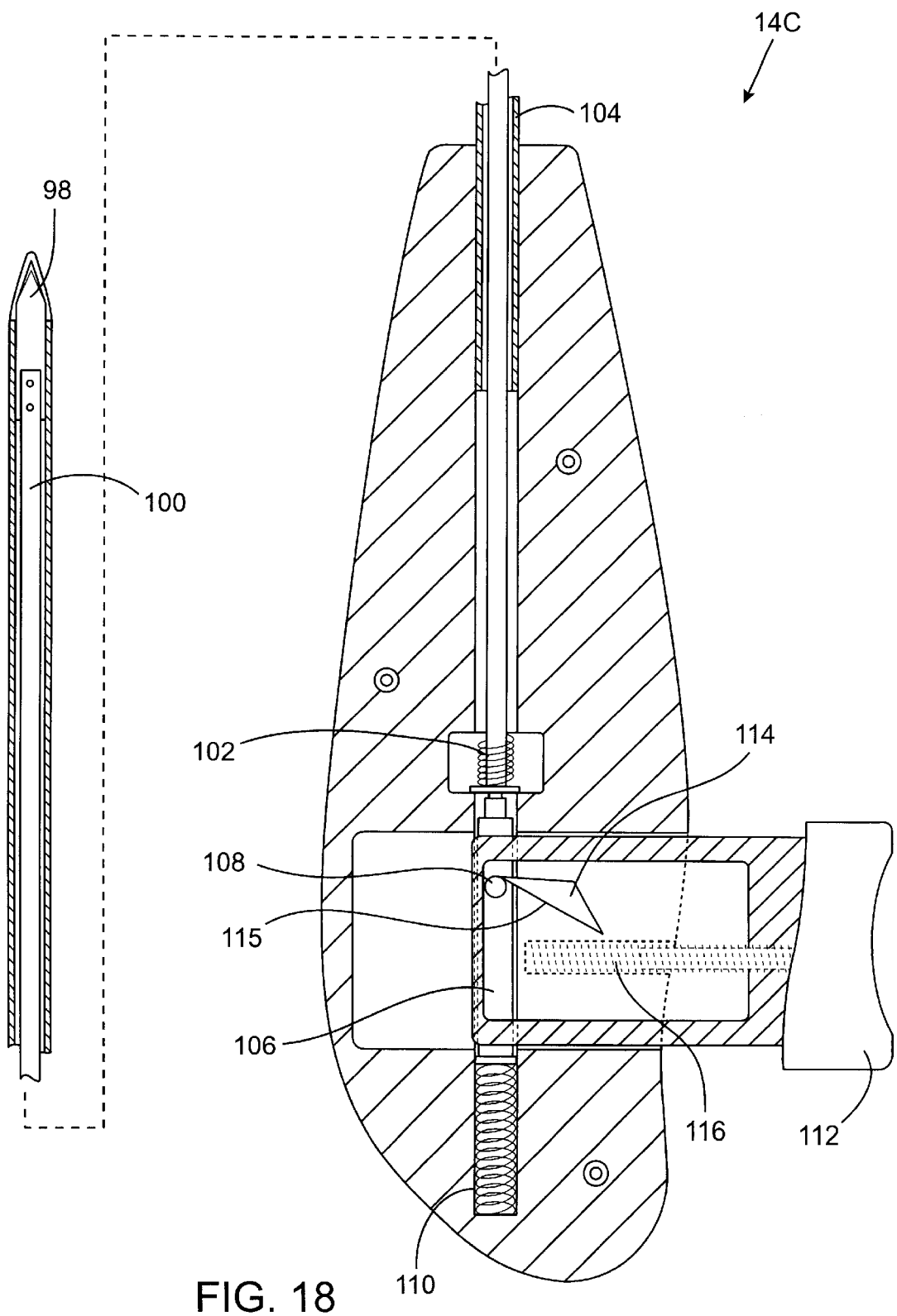
FIG. 18 shows a cross-sectional view of still another embodiment of the incisor of the present invention with the plunger in an undepressed position and the surgical element in a retracted position.
Figure 19:
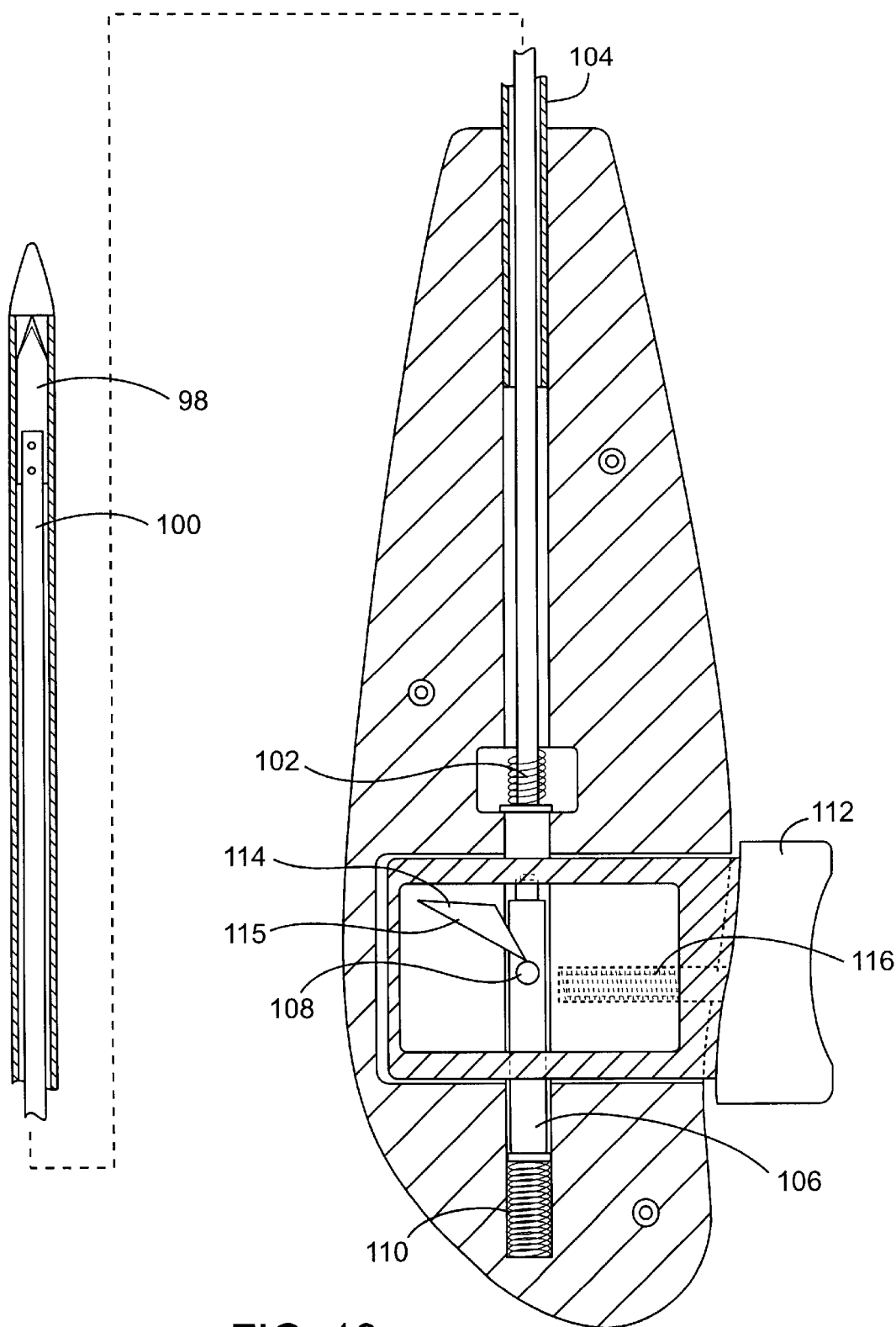
FIG. 19 shows a cross-sectional view of the incisor of FIG. 18 with the plunger in a partially depressed position and the surgical element in a retracted position.
Figure 20:
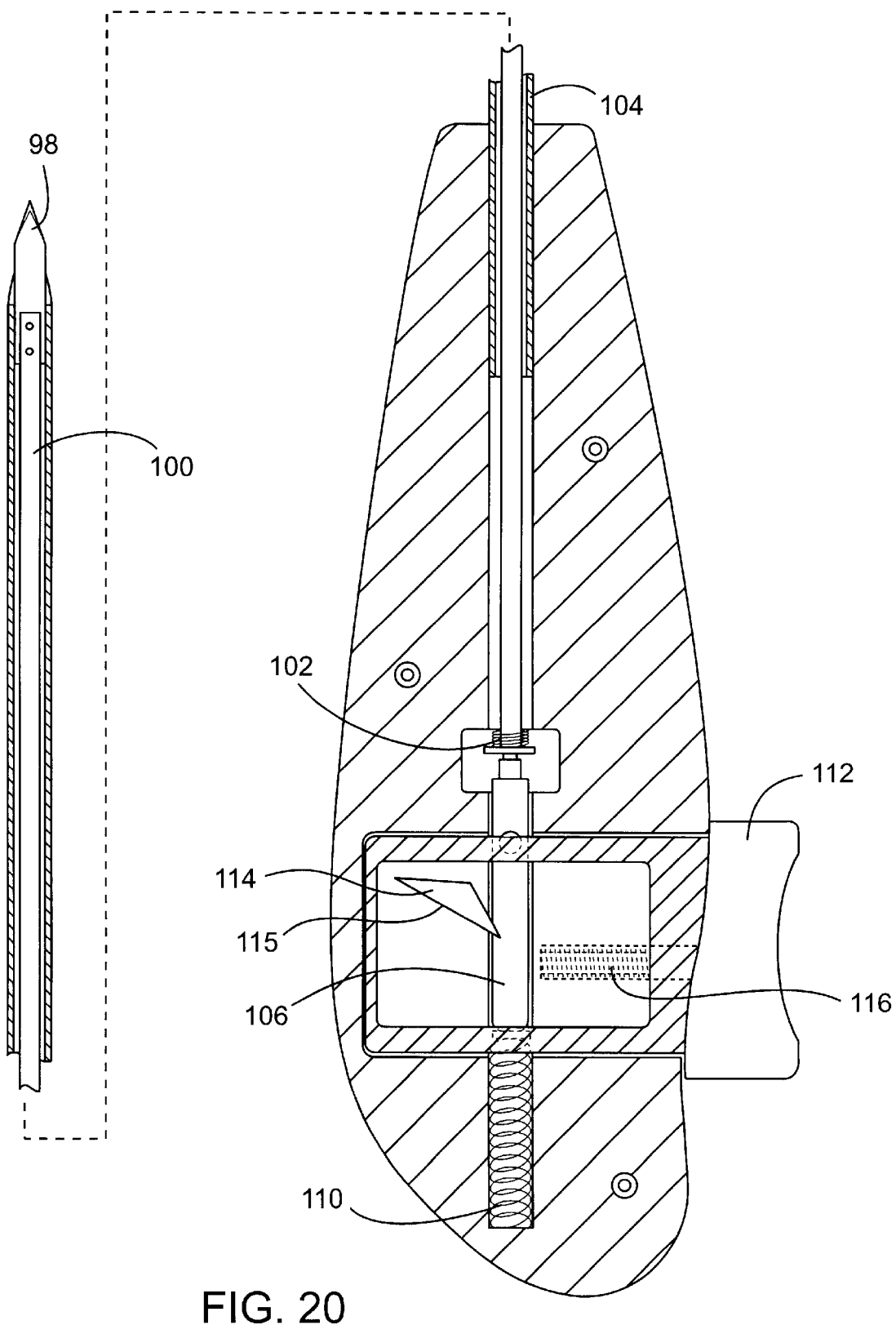
FIG. 20 shows a cross-sectional view of the incisor of FIG. 18 with the plunger in a fully depressed position and the surgical element in a deployed position.

Referring now to FIGS. 18–20, yet another incisor 14C is shown. The incisor shown comprises a mechanism which instantaneously advances and retracts the surgical element. The incisor 14C has a distal surgical element 98 coupled to a push rod 100. Similar to above, the surgical element 98 and the push rod 100 are biased by a push rod spring 102 in a retracted position within an elongate housing 104. A hammer 106 having a protrusion 108 is movable within housing 104 along substantially the same axis as the push rod 100, although unconnected with the push rod. A hammer compression spring 110 is disposed proximal of the hammer within housing 104 to provide the mechanism for actuating the hammer. A trigger 112 comprising a cam or ramp 114 is movable in a transverse direction relative to hammer 106 and is urged outwardly by a trigger spring 116 (FIG. 18). Angled surface 115 of the cam engages the protrusion 108 and forces the hammer 106 proximally against the compression spring 110 (FIG. 19). As the trigger 112 is advanced further, the cam 114 advances past the protrusion 108 and allows the hammer spring 110 to expand and force the hammer 106 distally so as to strike the proximal end of push rod 100. The impulse from the hammer 106 moves the push rod 100 and the surgical element 98 (i.e., a blade) instantaneously from its retracted position to a deployed position (FIG. 20). Because the push rod 100 and surgical element 98 are spring loaded to the retracted position, the push rod 100 and surgical element 98 are immediately urged from the deployed position back to the retracted position. The stiffness of springs 102 and 110 are selected such that the force of hammer 106 is sufficient to overcome the resistive force of spring 102 to drive rod 100 distally.

Use of the cannula, incisor and aortic occlusion device will now be described with reference to FIGS. 21A–21D. The description below is applicable to all the incisors 14, 14A, 14B, 14C described herein. Referring again to FIG. 9, before introduction of the cannula, a rib retractor 115 or other device can be used to form an opening in an intercostal space such as the fourth intercostal space. The opening through the intercostal space is used for access to perform a surgical procedure such as a valve repair or replacement or coronary bypass graft. The opening also provides direct access to the ascending aorta for control of the ascending aorta and to place purse string sutures in the aorta. The surgeon then places two purse-string sutures 39 around the site. The ends of the purse-string sutures are passed through tourniquet tubing which is used to tension the purse-string sutures. The purse string sutures are then passed through the slots 36 in the ring 34.

Figure 21A:
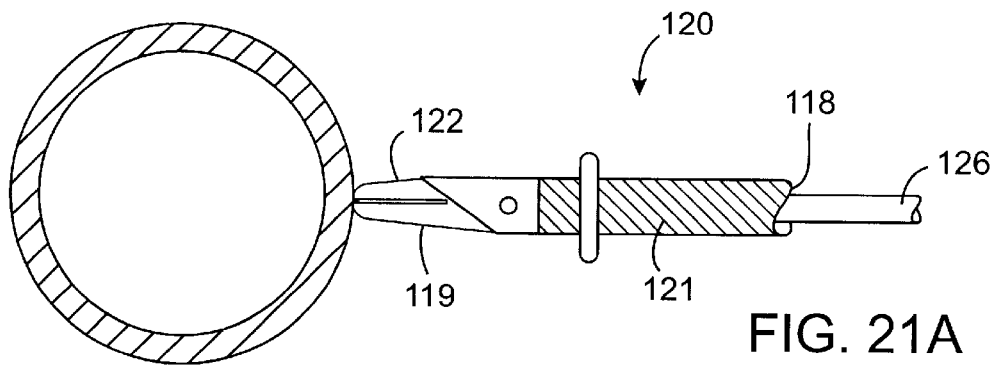
FIGS. 21A–21D illustrate a method of creating an incision in a vessel.
Figure 21B:
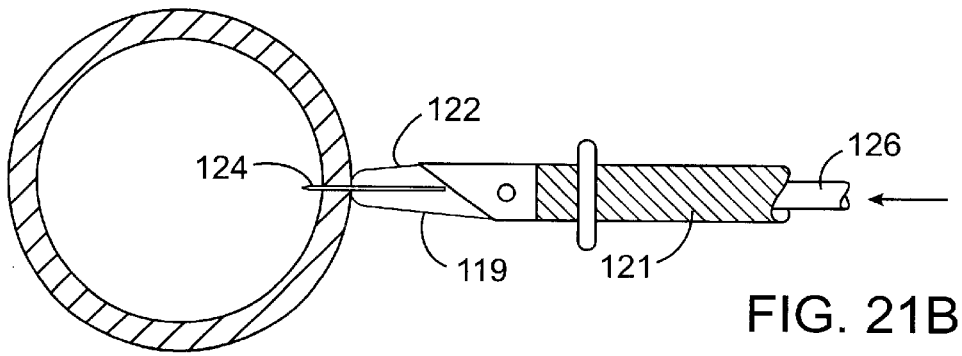
Figure 21C:
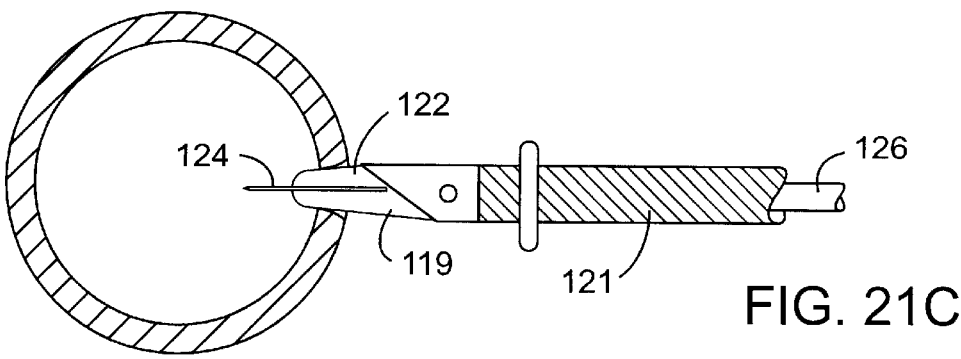
Figure 21D:
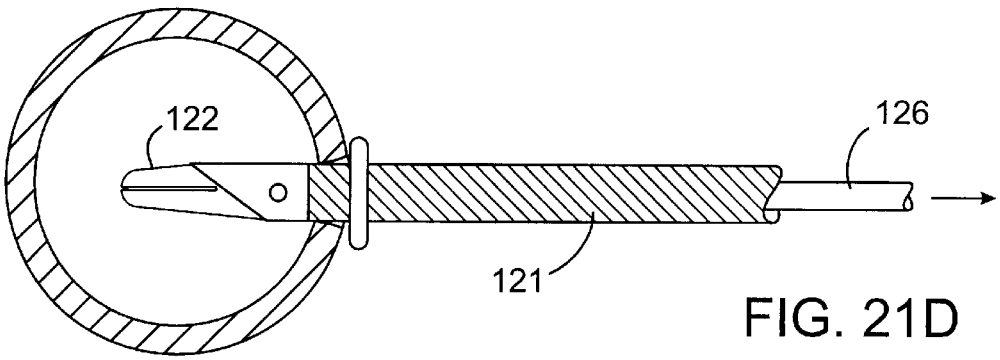

An incision is also created in the first or second intercostal space in which a trocar is positioned. The cannula 121 and incisor assembly 120 are then introduced through the trocar and advanced to the surface of the aorta with the incisor 119 positioned in the lumen 118 of the cannula 121. As illustrated in FIG. 21A, the cannula/incisor assembly are then advanced into contact with the aorta at the site now surrounded by the purse-string sutures. A light pressure can be applied with the traction features 123 of the distal tip 122 against the aorta to create dimples or indentations so as to help center the surgical element within the purse strings. The user then depresses the plunger to move the push rod 126 and the incising element 124 to a deployed position (FIG. 21B). As shown in FIGS. 21C and 21D, the incising element creates an incision in the wall of the vessel, and the incisor and the cannula tip are pushed through the wall until the ring contacts the adventitial surface of the vessel. As the trigger is further depressed, the incising element is automatically released and returns back to the retracted position. Once the cannula tip has been inserted into the blood vessel, the incisor can be removed and the aortic occluding device can be inserted through the hemostasis valve in the first arm and down the cannula (FIG. 10).

The systems and methods described above have been described in relation to the ascending aorta for clarity of understanding. The devices and methods of the present invention may have application in other parts of the aorta or heart and in other vessels and organs of the body. As changes and modifications will be obvious to those of skill in the art, the scope of the invention is limited solely by the following claims.

What is claimed is:

1. An apparatus for creating a vascular incision comprising:
   a body;
   a rod movable relative to the body and having a proximal end and a distal end;
   a surgical element disposed at the distal end of the rod, wherein the rod and surgical element are movable between a retracted position and a deployed position, wherein the rod and surgical element are biased in the retracted position;

an actuator coupled to at least one finger which engages the proximal end of the rod, wherein activation of the actuator advances the surgical element from the retracted position to the deployed position; and a ramp on the body to engage the finger as the rod and surgical element move to the deployed position, wherein the ramp disengages the finger from the proximal end of the rod to allow the surgical element to move to the retracted position.

2. The apparatus of claim 1 further comprising a return spring, wherein the actuator is movable between an undepressed position and a depressed position, wherein the return spring biases the actuator to the undepressed position.

3. The apparatus of claim 2 wherein the actuator defines a longitudinal axis and the rod defines a longitudinal axis, wherein the longitudinal axis of the actuator is substantially aligned with the longitudinal axis of the rod.

4. The apparatus of claim 1 wherein the actuator is coupled to multiple fingers which engage the rod.

5. The apparatus of claim 1 wherein the proximal end of the rod comprises an enlarged push rod cap.

6. The apparatus of claim 5 wherein the finger comprises a protrusion which engages the push rod cap.

7. The apparatus of claim 1 wherein the actuator is adapted to be engaged by a user's thumb or palm.

8. The apparatus of claim 1 wherein the body comprises finger grips adapted to be held by the user's fingers.

9. The apparatus of claim 1 wherein the finger disengages from the rod when the rod and surgical element have been advanced to a fully deployed position.

10. The apparatus of claim 1 wherein the finger is flexible and is resiliently biased radially inward towards the proximal end of the rod.

11. The apparatus of claim 1 wherein the disengagement of the finger from the rod creates an audible click.

12. The apparatus of claim 1 wherein the ramp forces the finger radially outward away from the proximal end of the rod.

13. The apparatus of claim 1 wherein the surgical element is a blade.

14. The apparatus of claim 13 wherein the blade has a width between approximately 4 mm and 6 mm.

15. The apparatus of claim 13 wherein a leading edge of the blade has two outwardly facing edges.

16. The apparatus of claim 13 wherein the rod is advanced at a 1:1 rate with the actuator.

17. The apparatus of claim 1 further comprising an elongate housing which extends distally from the body to encase the rod and surgical element.

18. The apparatus of claim 17 wherein the elongate housing and rod are flexible.

19. The apparatus of claim 17 wherein the elongate housing comprises a tapered distal tip having an opening to allow the surgical element to move between the retracted position and the deployed position.

* * * * *